(12) United States Patent
Hayashi

(10) Patent No.: US 7,216,983 B2
(45) Date of Patent: May 15, 2007

(54) OPHTHALMOLOGIC APPARATUS

(75) Inventor: Takefumi Hayashi, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 501 days.

(21) Appl. No.: 10/724,867

(22) Filed: Dec. 2, 2003

(65) Prior Publication Data
US 2004/0184000 A1 Sep. 23, 2004

(30) Foreign Application Priority Data
Dec. 4, 2002 (JP) ............................ 2002-351877

(51) Int. Cl.
*A61B 3/10* (2006.01)
(52) U.S. Cl. ...................................... 351/211; 351/221
(58) Field of Classification Search ........ 351/216–218, 351/233–236, 222, 246, 211, 221, 205; 359/13
See application file for complete search history.

(56) References Cited

U.S. PATENT DOCUMENTS 4,105,302 A 8/1978 Tate, Jr. .................... 351/7

5,589,956 A * 12/1996 Morishima et al. .......... 359/15
5,856,861 A * 1/1999 Hosoi et al. ................ 351/237

FOREIGN PATENT DOCUMENTS

| JP | 4-200435 | 7/1992 |
| JP | 2002-119471 | 4/2002 |

* cited by examiner

*Primary Examiner*—Hung Xuan Dang
(74) *Attorney, Agent, or Firm*—Armstrong, Kratz, Quintos, Hanson & Brooks, LLP

(57) ABSTRACT

According to the present invention, there is provided an ophthalmologic apparatus in which identifying power for the index or an index indicating state is improved to eliminate the confusion of a person to be examined, so that an eye examination time period can be shortened and the reliability of an eye examination can be improved. The ophthalmologic apparatus includes an index plate that displays an index, an index projecting optical system that projects the index to an eye to be examined, a variable cross cylinder that produces a pair of index indicating states of the index used for a cross cylinder test, a lamp and a liquid crystal screen that generate identifiers serving as identification information, and a dichroic mirror that combines the identifiers with the pair of index indicating states to be indicated to the eye to be examined.

3 Claims, 8 Drawing Sheets

Fig. 5
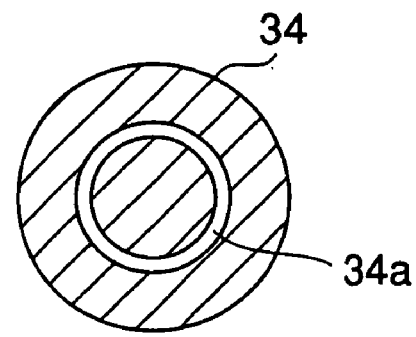
Fig. 6(A)
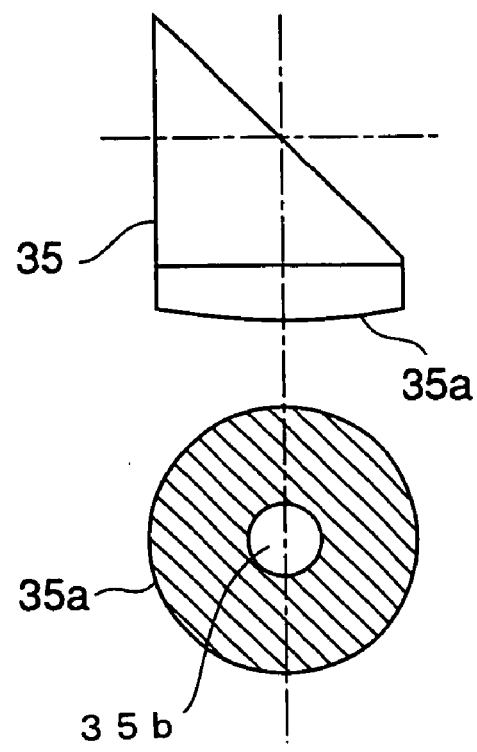
Fig. 6(B)

Fig. 7
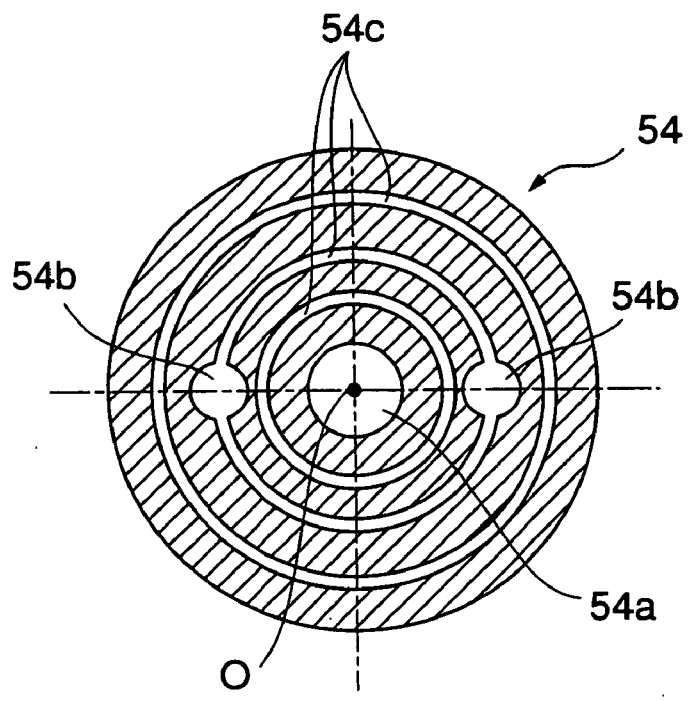
Fig. 8(A)  Fig. 8(B)
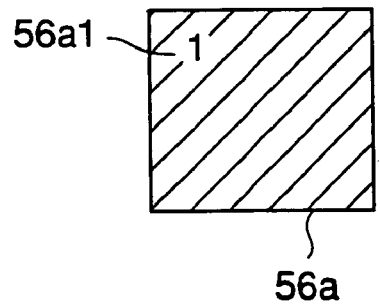 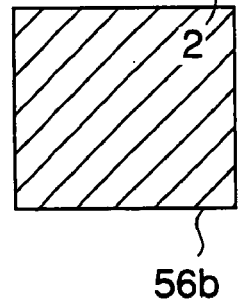

Fig. 9
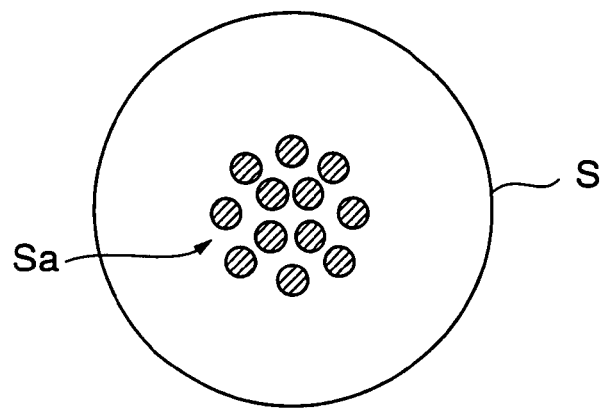
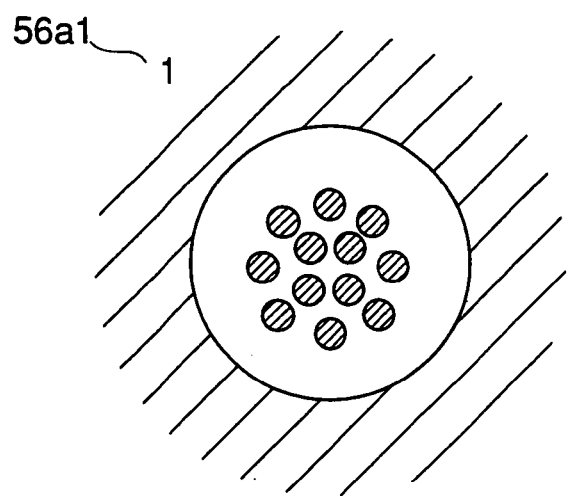
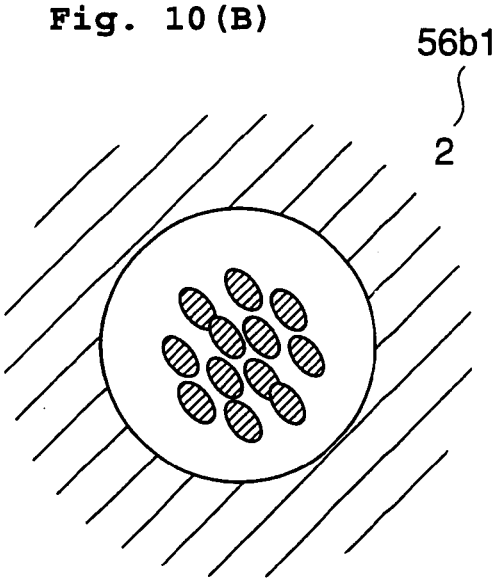

OPHTHALMOLOGIC APPARATUS

BACKGROUND OF THE INVENTION

1. Field of the Invention

The present invention relates to an ophthalmologic apparatus capable of conducting at least subjective measurement of the refractive power of an eye to be examined.

2. Description of the Related Art

Up to now, with respect to measurement of the refractive power of an eye to be examined (ocular refractive power), a subjective eye examination for conducting measurement based on responses of a person to be examined to various indexes such as Landolt rings and an objective eye examination which is conducted without using the responses of the person to be examined are used in combination. Now, an ophthalmologic apparatus capable of effectively using both the subjective eye examination and the objective eye examination become widely available. Therefore, attempts of improvement in efficiency and reliability of the examination, size reduction of the apparatus etc. are conducted.

Also, in order to further improve the efficiency of the examination, an ophthalmologic apparatus in which the person to be examined him/herself can conduct eye examination has been developed. As such an ophthalmologic apparatus, an ophthalmologic apparatus described in, for example, JP 2002-119471 A (specification paragraph [0026] and FIG. 3) has been known. The ophthalmologic apparatus described in JP 2002-119471 A can conduct both the subjective eye examination and the objective eye examination. A moving image and a still image which show an measurement order are displayed on a monitor device under the control of a computer and the measurement order is also announced, so that the person to be examined can be automatically guided.

It is greatly expected that the automated ophthalmologic apparatus become widely available in the future. It is a fact that a problem to be solved to achieve the wide use remains. For example, when a plurality of indexes or a plurality of index indicating states (states of index images projected to the eye to be examined) are made to appear in the eye to be examined and an examination is performed based on a result in which the person to be examined conducts subjective comparison and determination with respect to the visibility of the plurality of indexes and the like, it is difficult for the person to be examined to distinguish an index, which actually appears in the eye, among from the plurality of indexes and the like. An example thereof is given. In a cross cylinder test (hereinafter referred to as a CC test) which is a general method of an astigmatic examination, an examination is performed based on a result in which the person to be examined conducts comparison and determination as to clearly recognize which of a pair of index indicating states produced by reversing positive and negative refractive powers of the cross cylinder. In this time, the person to be examined becomes confused by not being able to distinguish which is the index indicating state for the power produced in many cases. Therefore, this causes that a time period required for the eye examination is lengthened and becomes a factor that the reliability of the eye examination is deteriorated.

Also, even in the case of the CC test which is conducted in the presence of an examiner and/or an assistant, it is difficult for the person to be examined to smoothly select among the index indicating states as in the above-mentioned case.

Note that, there has been known an ophthalmologic apparatus in which identification information visually identifiable is provided to each of a pair of cylindrical lenses used for the CC test and a pair of operational direction indexes corresponding to the identification information are provided to an astigmatic power switching operating unit for conducting astigmatic power switching and an astigmatic axis operating unit for conducting astigmatic axis switching, which are operated by the examiner, so that the astigmatic power switching operating unit and the astigmatic axis operating unit can be operated toward the operational direction index corresponding to any one of the identification information recognized by the person to be examined (see JP 2992337 B (claims)). According to this ophthalmologic apparatus, the response of the person to be examined to the identification information directly becomes to mean the operational direction index of the astigmatic axis operating unit or the astigmatic power switching operating unit. Therefore, the examiner can accurately and speedily conduct astigmatic examination.

But, the identification information only contributes to improvement in operationality of the apparatus operated by the examiner, and a labor and a cost are required for providing the identification information to each of a large number of cylindrical lenses.

SUMMARY OF THE INVENTION

The present invention has been made in view of the above-mentioned circumstances. Therefore, an object of the present invention is to provide an ophthalmologic apparatus in which identifying power for an index or an index indicating state is improved to eliminate the confusion of a person to be examined, so that an eye examination time period can be shortened and the reliability of an eye examination can be improved.

In order to attain the above-mentioned object, according to a first aspect of the present invention, there is provided an ophthalmologic apparatus provided with index locating means capable of selectively locating an index for eye examination and an index projecting optical system that successively indicates index images to an eye to be examined by changing an index image of the index selectively located by the index locating means, the ophthalmologic apparatus including: identification information generating means for generating identification information for making a person to be examined identify each of the index images which are successively indicated by the index projecting optical system; and an identification information combining member that combines the identification information generated by identification information generating means with each of the index images to be indicated to the eye to be examined.

Further, according to a second aspect of the present invention, the ophthalmologic apparatus according to the first aspect further includes identification information changing means for changing the identification information generated by identification information generating means in accordance with changing of the index image which is indicated to the eye to be examined by the index projecting optical system.

Further, according to a third aspect of the present invention, in the ophthalmologic apparatus according to the second aspect, the index projecting optical system includes a cross cylinder that produces a pair of index images by providing predetermined astigmatic power to the index located by the index locating means in order to conduct an astigmatic examination on the eye to be examined, and the identification information changing means changes the identification information generated by identification information generating means in accordance with switching of the pair of the index images which are indicated to the eye to be examined by the cross cylinder.

BRIEF DESCRIPTION OF THE DRAWINGS

In the accompanying drawings:

FIG. 5 is a schematic view showing a structure of a pupil ring diaphragm included in the ophthalmologic apparatus;

FIGS. 6A and 6B are schematic views showing a structure of a triangular prism included in the ophthalmologic apparatus;

FIG. 7 is a schematic view showing a structure of a ring pattern included in the ophthalmologic apparatus;

FIGS. 8A and 8B are schematic views showing screens displayed on a liquid crystal screen included in the ophthalmologic apparatus;

FIG. 9 is a schematic view showing an index included in the ophthalmologic apparatus;

FIGS. 10A and 10B are schematic views showing indicating states of the index to an eye to be examined, which is included in the ophthalmologic apparatus;

DETAILED DESCRIPTION OF THE PREFERRED EMBODIMENTS

Hereinafter, preferred embodiments of the present invention will be specifically described with reference to the drawings.

First Embodiment

[Entire Structure]

Figure 1:
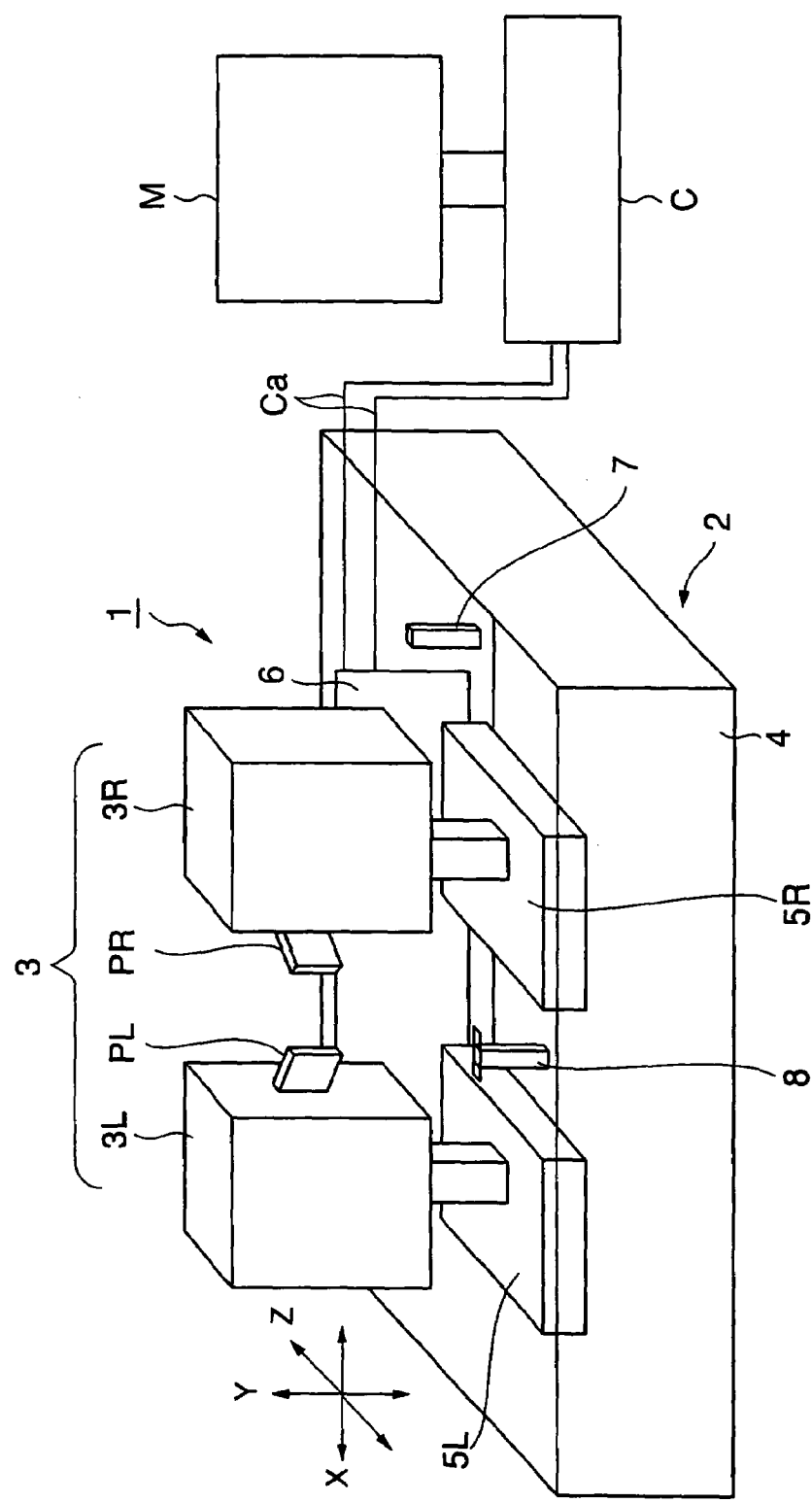
FIG. 1 is a schematic perspective view showing an entire structure of an ophthalmologic apparatus according a first embodiment of the present invention.

FIG. 1 is a perspective view showing an entire structure of an ophthalmologic apparatus 1 according a first embodiment of the present invention. The ophthalmologic apparatus 1 is an apparatus capable of conducting an astigmatic examination in addition to subjective and objective refractive power measurements in a situation in which an eye examination is conducted on a person to be examined alone or on a plurality of persons to be examined accompanied by an assistant who guides the plurality of persons to be examined. The eye examination is automatically conducted by the ophthalmologic apparatus 1 in accordance with predetermined processes. First, an approximate value of the refractive power of an eye to be examined is obtained by the objective refractive power measurement and the subjective measurement is conducted based on the obtained approximate value. Subsequently, astigmatic power and the like are obtained by conducting an astigmatic examination and then spherical power is adjusted. Finally, a vision examination is conducted using the obtained astigmatic power. Note that, it is needless to say that the ophthalmologic apparatus 1 can be used in the case where the eye examination is conducted in a state in which an examiner has one-on-one contact with the person to be examined.

Figure 4:
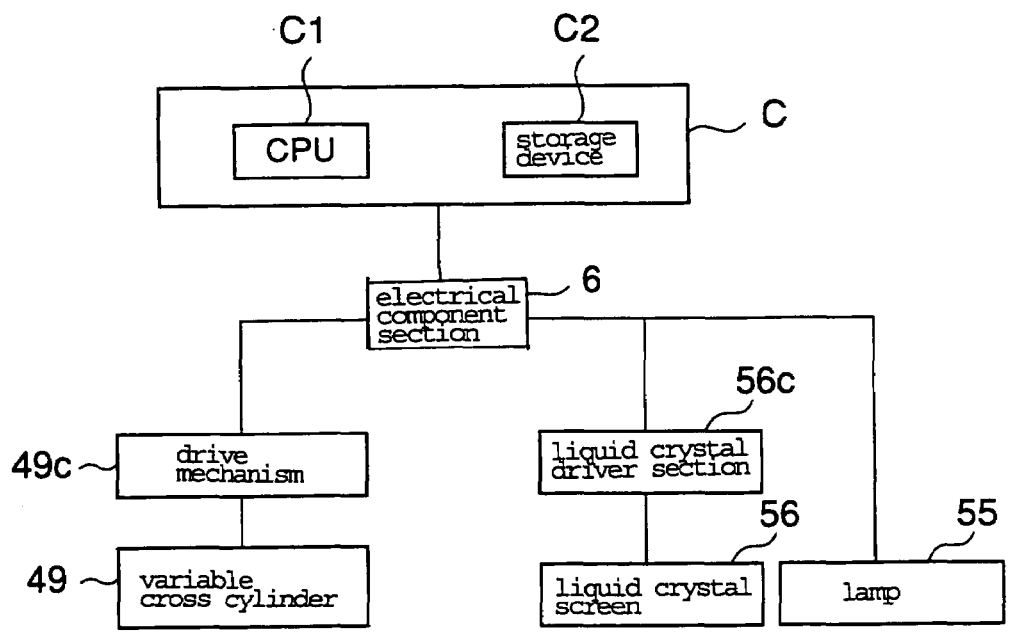
FIG. 4 is a block diagram showing a schematic structure of the ophthalmologic apparatus.

The ophthalmologic apparatus 1 is connected with a computer C through a cable Ca. As shown in FIG. 4 described later, the computer C includes CPU C1 serving as an arithmetic processing unit and a storage device C2 such as a hard disk or a ROM. The CPU C1 controls the operation of the ophthalmologic apparatus 1 in accordance with an application software stored in the storage device C2. The application software includes a program for causing the ophthalmologic apparatus 1 to automatically conduct the eye examination, that is, a program for causing the ophthalmologic apparatus 1 to conduct respective processes such as the objective refractive power measurement, the subjective refractive power measurement, the astigmatic examination, the spherical power adjustment, and the final vision examination. Note that, when there are an examiner and/or an assistant (hereinafter referred to as "an examiner and the like"), various operations of the ophthalmologic apparatus 1 can be controlled by an input operation of the examiner and the like using an input unit (not shown) such as a keyboard or a mouse of the computer C. In addition, the computer C is connected with a monitor M that displays an anterior ocular segment of the person to be examined, measurement data thereof, personal data thereof, and the like.

The ophthalmologic apparatus 1 includes a main body 2 and a head section 3 composed of a pair of heads. The head section 3 is composed of a left eye head 3L and a right eye head 3R. Bases 5L and 5R that separately actuate the left eye head 3L and the right eye head 3R up and down, back and forth, and from side to side (that is, three-dimensionally) and an electrical component section 6 that operates respective units of the ophthalmologic apparatus 1 according to control signals transmitted from the computer C are housed in a case 4. A joystick 7 operated by the person to be examined and a chin rest stand 8 for holding the chin of the person to be examined are provided on the upper surface (shown perspectively in the figure) of the case 4.

Figure 2:
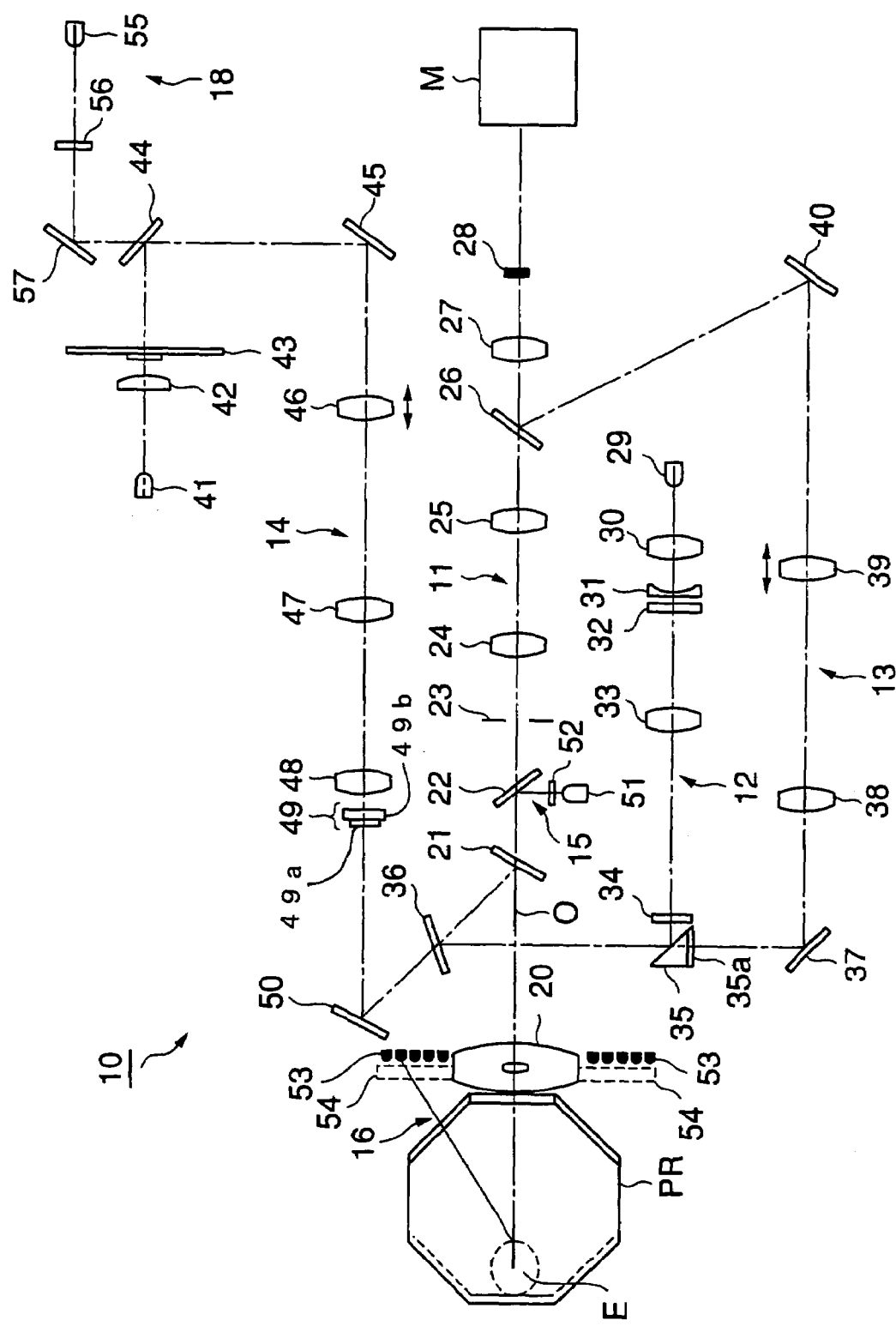
FIG. 2 shows a structure of an optical system of the ophthalmologic apparatus.

An optical system 10 for conducting an eye examination, which includes various lenses, various light sources, and various mirrors as shown in FIG. 2 described later, is incorporated in the head section 3. A prism PL which is disposed to oppose a left eye of the person to be examined is provided to the left eye head 3L. A prism PR which is disposed to oppose a right eye of the person to be examined is provided to the right eye head 3R.

[Structure of Optical System]

Hereinafter, a structure of the optical system which is incorporated in the head section 3 will be described in detail. Here, the optical systems which are incorporated in the left eye head 3L and the right eye head 3R are symmetrically provided and have substantially no difference. Therefore, only the optical system incorporated in the right eye head 3R will be described and the description with respect to the optical system of the left eye head 3L is omitted. In addition, hereinafter, an eye to be examined E indicates the right eye of the person to be examined.

Figure 3:
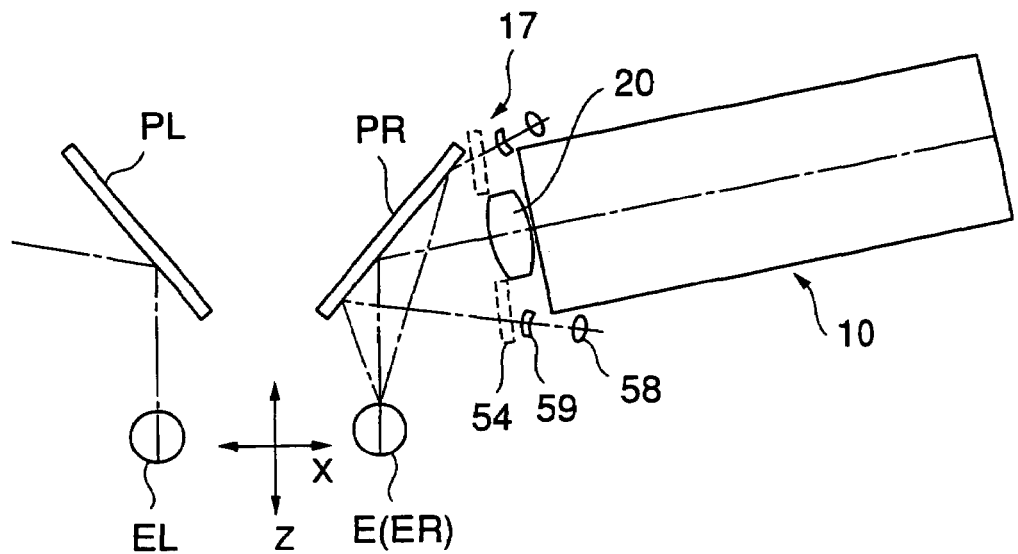
FIG. 3 shows a structure of an optical system of the ophthalmologic apparatus.

FIGS. 2 and 3 show the structure of the optical system 10 incorporated in the right eye head 3R. Note that FIG. 3 is a top view. In addition, FIG. 4 is a block diagram showing a structure for driving (a part of) the optical system 10. The optical system 10 includes an image pickup optical system 11, a measurement light flux projecting optical system 12, a light receiving optical system 13, an index projecting optical system 14, an X-Y alignment optical system 15, a ring pattern projecting optical system 16, a Z-alignment optical system 17, and an identifier generating optical system 18.

The image pickup optical system 11 is an optical system for picking up an image of an anterior ocular segment of the eye to be examined E using a CCD 28 in the case of: observing the anterior ocular segment; conducting alignment between the eye to be examined E and the right eye head 3R; or measuring a cornea curvature distribution. Note that the anterior ocular segment image picked up by the CCD 28 is displayed on the monitor M. The image pickup optical system 11 includes an objective lens 20, dichroic mirrors 21 and 22, a diaphragm 23, relay lenses 24 and 25, a dichroic mirror 26, an imaging lens 27 that forms the anterior ocular segment image onto the CCD 28, and the CCD 28 serving as an image pickup unit in this order. Here, the diaphragm 23 is a so-called telecentric diaphragm which is disposed at the focal point of the objective lens 20. A light ray passing through the center of the diaphragm 23 becomes parallel to an optical axis O of the ophthalmologic apparatus on the eye to be examined E.

The measurement light flux projecting optical system 12 is an optical system for projecting an index for measuring the objective refractive power of the eye to be examined E thereto. The measurement light flux projecting optical system 12 includes a measurement light source 29 such as an infrared LED, a collimator lens 30, a conical prism 31, a measurement ring target 32 serving as an index, a relay lens 33, a pupil ring diaphragm 34, a triangular prism 35, dichroic mirrors 36 and 21, and the objective lens 20 in this order. Note that, as shown in FIG. 5, etching is made on a surface of the pupil ring diaphragm 34 such that a ring-shaped transmission portion 34a transmitting a light flux from the measurement light source 29 is formed. In addition, the surface is positioned to conjugate with the eye to be examined E. Therefore, a ring-shaped projection image can be projected onto the eye to be examined E by the light flux from the measurement light source 29. FIGS. 6A and 6B show a structure of the triangular prism 35. FIG. 6A is a side view and FIG. 6B is a bottom view. As shown in FIGS. 6A and 6B, etching is made on a bottom surface 35a of the triangular prism 35. A transmission portion 35b having a size capable of transmitting a light flux, which is reflected on the eye to be examined E and transmits through the light receiving optical system 13 described later in detail, is formed in the bottom surface 35a. Note that the triangular prism 35 is disposed such that the bottom surface 35a is positioned to conjugate with the pupil of the eye to be examined E.

The light receiving optical system 13 is an optical system for receiving a light flux which is reflected on the eye to be examined E in the case where the refractive power of the eye to be examined E is measured. With respect to the structure of the light receiving optical system 13 includes the objective lens 20, the dichroic mirrors 21 and 36, (the transmission portion 35b formed in the center of) the triangular prism 35, a reflection mirror 37, a relay lens 38, a movable lens 39 which is driven by a pulse motor (not shown) and moves according to the refractive power of the eye to be examined E, a reflection mirror 40, the dichroic mirror 26, the imaging lens 27, and the CCD 28 in this order.

The index projecting optical system 14 is an optical system for projecting various indexes such as indexes used for the vision examination and fixed indexes to the eye to be examined E and for conducting a fogging operation. The index projecting optical system 14 includes a lamp 41 serving as a light source, a collimator lens 42, an index plate 43 serving as an index locating unit in which visible indexes are selectively locatable, a dichroic mirror 44, a reflection mirror 45, a movable lens 46 which is driven by a pulse motor (not shown) and provided to be moveable in order to apply various refractive powers to the eye to be examined E upon the eye examination, relay lenses 47 and 48, a variable cross cylinder 49 for conducting an astigmatic correction of the eye to be examined E, a reflection mirror 50, the dichroic mirrors 36 and 21, and the objective lens 20 in this order. In addition to various indexes such as Landolt rings and E characters for (subjective) vision examination, indexes for red/green test, and indexes for cross cylinder test, fixed indexes such as landscape pictures are located on the index plate 43 to be selectively displayable. Further, in the case where the movable lens 46 is moved toward the eye to be examined E, the refractive power can be negatively changed. On the other hand, when the movable lens 46 is moved in a direction apart from the eye to be examined E, the refractive power can be positively changed. Therefore, it is possible to conduct the fogging operation.

The variable cross cylinder 49 includes a cylindrical lens 49a having positive refractive power in a direction orthogonal to an axis of the cylinder and a cylindrical lens 49b having negative refractive power in the direction orthogonal to the axis of the cylinder. The cylindrical lens 49a and the cylindrical lens 49b are separately rotated at an arbitrary angle by a drive mechanism 49c such as a pulse motor as shown in FIG. 4. In a cross cylindrical test, the cylindrical lenses 49a and 49b are disposed such that the axes thereof are orthogonal to each other, thereby the positive and negative refractive powers orthogonal to each other (predetermined quantity of astigmatism) are produced in the index image of an index projected to the eye to be examined E. Further, the cylindrical lenses 49a and 49b are rotated to produce astigmatic power in which the positive and negative directions of the refractive power are reversed. With this state, the index image appears in the eye to be examined E. Here, assume that a combination of the index image before the reverse and the index image after the reverse is called "a pair of index images". In addition, it is defined that "the quantity of astigmatism" indicates two factors specifying an astigmatism of the eye to be examined, that is, cylindrical power and an angle of an astigmatic axis.

The X-Y alignment optical system 15 is an optical system for conducting an alignment of the right eye head 3R with the eye to be examined E in X- and Y-directions. Here, assume that the horizontal direction is the X-direction, the perpendicular direction is the Y-direction, and the depth direction of the ophthalmologic apparatus 1 is a Z-direction (see FIGS. 1 and 3). The X-Y alignment optical system 15 includes an LED 51 serving as an illumination light source used to conduct the alignment in the X- and Y-directions, a diaphragm 52 serving as an index for alignment, the dichroic mirrors 22 and 21, and the objective lens 20 in this order.

The ring pattern projecting optical system 16 is an optical system for projecting a ring pattern used to measure a cornea curvature distribution to the eye to be examined E and also serves to illuminate the eye to be examined E for observation. The ring pattern projecting optical system 16 includes an LED group 53 serving as a light source and a disk-shaped ring pattern 54 arranged about the optical axis O in this order. As shown in FIG. 7, etching is concentrically made on a surface of the ring pattern 54 (hatched region in FIG. 7 to form a central transmission portion 54a, an alignment light flux transmission portion 54b, and a measurement light flux transmission portion 54c, which are used for transmitting various light fluxes. As shown in FIGS. 2 and 3, the central transmission portion 54a is disposed to surround the objective lens 20 and transmits all light fluxes passing through the above-mentioned optical system other than the ring pattern projecting optical system 16. The alignment light flux transmission portion 54b which is composed of a pair of transmission regions is a region provided for transmitting a light flux from a light source (LED 58 described later) of the Z-alignment optical system 17. As shown in FIG. 2, the measurement light flux transmission portion 54c composed of a plurality of ring-shaped transmission portions which are concentrically provided transmits light fluxes from the LED group 53, thereby producing concentrically formed light fluxes which are projected to the eye to be examined E upon measurement of the cornea curvature distribution.

The Z-alignment optical system 17 as shown in FIG. 3 includes a pair of LEDs 58, a pair of lenses 59, and (the alignment light flux transmission portion 54b of) the ring pattern 54 in this order, and is used to conduct a distance adjustment (Z-directional alignment) between the eye to be examined E and the right eye head 3R.

The identifier generating optical system 18 includes a lamp 55 serving as a light source and a liquid crystal screen 56. As shown in FIG. 4, the lamp 55 is turned on or turned off by the action of the electrical component section 6 operated in accordance with a control signal from the computer C. The liquid crystal screen 56 is connected with a liquid crystal driver section 56c that drives the liquid crystal screen 56. A numeral, a character, a symbol, or the like (hereinafter referred to as a numeral or the like) such as "1" 56a1 on an end region of a screen 56a shown in FIG. 8A or "2" 56b1 on an end region of a screen 56b shown in FIG. 8B is selectively displayed on the liquid crystal screen 56 by the action of the electrical component section 6 that receives a control signal from the computer C. In other words, the identifier generating optical system 18 illuminates the above-mentioned numeral or the like which is displayed on the liquid crystal screen 56 by using the lamp 55 to produce a light flux for projecting the above-mentioned numeral or the like to the eye to be examined E. As shown in FIG. 2, the dichroic mirror 44 is used for combining the light flux for projecting the above-mentioned numeral or the like which is generated by the identifier generating optical system 18 with the light flux for indicating an index image which is transmitted through the index projecting optical system 14. In other words, (in the case where the lamp 55 and the liquid crystal screen 56 each are in an operating state,) the index image appears in the eye to be examined E in a state in which the above-mentioned numeral or the like is attached to the index image.

Also, as shown in FIG. 4, the electrical component section 6 is connected with the drive mechanism 49c that drives the variable cross cylinder 49. The application software stored in the storage device C2 includes a program for simultaneously controlling the variable cross cylinder 49, the lamp 55, and the liquid crystal screen 56. When a control signal from the computer C is received, the electrical component section 6 operates the identifier generating optical system 18 such that a different numeral or the like is generated for each of a pair of index images which are indicated by the reverse action of the variable cross cylinder 49. For example, the electrical component section 6 starts the operation of the drive mechanism 49c for the variable cross cylinder 49, and simultaneously turns on the lamp 55 and starts the operation of the liquid crystal driver section 56c so as to produce the screen 56a shown in FIG. 8A on the liquid crystal screen 56. Then, the electrical component section 6 operates the drive mechanism 49c such that the variable cross cylinder 49 conducts the reverse action, and simultaneously sends a signal to the liquid crystal driver section 56c to produce the screen 56b shown in FIG. 8B on the liquid crystal screen 56. As a result, "1" 56a1 is attached to the index image produced before the reverse of the variable cross cylinder 49 and "2" 56b1 is attached to the index image produced after the reverse thereof. With such a state, the index image appears in the eye to be examined E, so that the person to be examined can easily identify the index image. Regarding such a fact, the above-mentioned numeral or the like is called "an identifier" (identification information). The identifier generating optical system 18 that generates the identifier acts as an identification information generating means. The dichroic mirror 44 acts as an identification information combining member. The electrical component section 6 operates as an identification information changing means. Here, the numeral or the like which is displayed on the liquid crystal screen 56, a light flux produced by illuminating the numeral or the like using the lamp 55, and a projection image of the light flux onto the eye to be examined E are generically called an identifier.

Assume that a prism PR is included in each of the above-mentioned optical systems 11 to 18. In the case where the travelling direction of a light flux transmitting through the respective optical systems is changed, the prism PR acts so as to adequately input and output the light flux with respect to the eye to be examined E.

[Eye Examination Process in Ophthalmologic Apparatus and Operation of Ophthalmologic Apparatus]

Subsequently, an eye examination process which is conducted using the ophthalmologic apparatus 1 having the above-mentioned structure and an operation of the ophthalmologic apparatus 1 during the eye examination process will be described. Note that, hereinafter, only the right eye head 3R is described. Unless otherwise mentioned, the right eye head 3R is described instead of the left eye head 3L in view of the symmetry in the arrangements of the optical systems.

First, the person to be examined sits on a chair (not shown) to be opposed to an eye examination table (not shown) on which the ophthalmologic apparatus 1 is placed. The height of the eye examination table is adjustable, and the height of the eye examination table is adjusted so as to align the prism PL and PR with the eye to be examined E. Next, when the application software for eye examination is started, eye examination procedures to be conducted by the ophthalmologic apparatus 1 are displayed on the monitor M in succession. In addition, a practice screen for practicing using the ophthalmologic apparatus 1 is displayed. Note that the practice screen can be skipped for the person to be examined who is skilled in the operation. After the practice, a voice guide is produced from a speaker (not shown) of the ophthalmologic apparatus 1 instructing the person to be examined to rest the chin on the chin rest stand 8. When the chin of the person to be examined is rested on the chin rest stand 8 in response to the voice guide, the process goes to a step of conducting an alignment for accurate eye examination.

(Alignment Process)

Before an actual eye examination is conducted, an alignment of the head section 3 with the eye to be examined E is conducted. In order to conduct the alignment, the ring pattern projecting optical system 16, the X-Y alignment optical system 15, and the Z-alignment optical system 17 are operated. More specifically, first, the LED group 53 is turned on to serve as an observation illumination of the eye to be examined E, illuminating the eye to be examined E with diffused light related to the ring pattern 54. In addition, the LED 51 is turned on to project an X-Y alignment light flux to the eye to be examined E through the X-Y alignment optical system 15. Further, the pair of LEDs 58 are turned on to project a Z-directional alignment light flux to the eye to be examined E through the Z-alignment optical system 17. At this time, reflected light produced by reflecting on the cornea the light fluxes incident from the three optical systems into the eye to be examined E is imaged onto the CCD 28 through the image pickup optical system 11, so that the anterior ocular segment image of the eye to be examined E is displayed on the monitor M. The electrical component section 6 calculates an accurate alignment position based on a projection image onto the eye to be examined E, which is produced by the ring pattern 54 and the LED 58 and picked up by the CCD 28. In addition, the electrical component section 6 controls displacements of the bases 5L and 5R in X-, Y-, and Z-directions in accordance with the alignment position and moves the head section 3 to the accurate alignment position.

Hereinafter, the eye examination is conducted. With respect to the eye examination process, first, the objective eye examination is conducted; second, vision measurement is conducted for each eye based on data obtained by the objective eye examination; third, a red/green test is conducted for each eye to obtain spherical power for each eye; fourth, a cross cylinder test is conducted to obtain astigmatic power and an astigmatic axis angle; fifth, the spherical powers of both eyes are balanced; and last, vision measurement is conducted on both eyes using the spherical powers, the astigmatic powers, and the astigmatic axis angles, which are obtained as described above.

(Objective Eye Examination Process)

After the alignment is completed, in order to fix the eye to be examined E, a fixed index is displayed on the index plate 43 and the lamp 41 is turned on to project the fixed index to the eye to be examined E. After the fixation is completed, first, a cornea curvature distribution is measured. The cornea curvature distribution is measured using the reflection light flux of the diffused light related to the ring pattern 54 and a reflection brightness point related to the LED 51, which are imaged onto the CCD 28. For example, the cornea curvature distribution can be calculated by measuring distances between the reflection brightness point related to the LED 51 and respective rings of a projection image related to the ring pattern 54. In addition, the cornea curvature distribution may be calculated from distances between the central point of the ring pattern 54 and the respective rings.

Next, the refractive power of the eye to be examined E is measured. Therefore, the measurement light source 29 is turned on to project to the eye to be examined E a ring-shaped light flux transmitting through the transmission portion 34a of the pupil ring diaphragm 34. The ring-shaped light flux reflected on the eye fundus of the eye to be examined E has its shape distorted by the refractive power of the eye to be examined E. The distorted ring-shaped light flux is imaged onto the CCD 28 through the light receiving optical system 13. The refractive power of the eye to be examined E is calculated by analyzing the distortion of the picked up ring-shaped light flux.

In order to improve measurement precision of the refractive power of the eye to be examined E, a unit which is composed of the measurement light source 29, the collimator lens 30, the conical prism 31, and the measurement ring target 32 and the movable lenses 39 and 46 may be moved so that a size of the ring-shaped light flux which is picked up by the CCD 28 approaches a predetermined reference size. In this case, the measurement is conducted two times. In other words, an approximate value of the refractive power of an eye to be examined E is obtained by first measurement and converted into the moving amount of the above-mentioned unit and the like. Second measurement is conducted in a state in which the above-mentioned unit and the like are moved by the converted moving amount.

By conducting the process up to now, the objective eye examination is completed. The subsequent subjective eye examination is conducted using the data obtained by the objective eye examination as reference values.

(One Eye Vision Measurement Process)

In a first process of the subjective eye examination, the vision measurement is conducted for each eye using refractive power data obtained by the objective eye examination. Therefore, first, the display content of the index plate 43 is changed to the Landolt ring to indicate the Landolt ring to the eye to be examined E. An index such as an E character may be indicated. The person to be examined operates the joystick 7 to answer the "break" direction of the Landolt ring. A signal indicating a direction in which the joystick 7 is tilted is transmitted to the computer C. The direction in which the joystick 7 is tilted is compared with the break direction of the indicated Landolt ring. If the answer is correct (both directions coincide with each other), the Landolt ring displayed on the index plate 43 is changed to a Landolt ring having a high vision value. On the other hand, if the answer is incorrect (both directions do not coincide with each other), a vision value of the Landolt ring is reduced. Here, the number of correct answers and the number of incorrect answers which are required to change the vision value are arbitrarily set by an examiner or an assistant.

(Red/Green Test Process)

Subsequently, the index displayed on the index plate 43 is changed and a red/green test is conducted. With respect to a red/green test index, as in a general test, an index in which a numeral (for example 6) is displayed on a red background is located on the left side and an index in which a numeral (for example 9) is displayed on a green background is located on the right side. The person to be examined selects the side in which the numeral can be clearly recognized and tilts the joystick 7 in the selective direction. That is, when the numeral on the red background is clearly recognized, the joystick 7 is tilted to the left. On the other hand, when the numeral on the green background is clearly recognized, the joystick 7 is tilted to the right. A signal indicating a direction in which the joystick 7 is tilted is transmitted to the computer C. When the red background side is selected, the movable lens 46 is moved toward the eye to be examined E so as to change the spherical power by −0.25D. When the green background side is selected, the movable lens 46 is moved in the reverse direction so as to change the spherical power by +0.25D. When the person to be examined changes the answer from the red background side to the green background side or from the green background side to the red background side, the red/green test is completed and the spherical power when the red background side is selected is determined as a measurement value. Note that whether the spherical power when the red background side is selected or the spherical power when the green background side is selected is determined as the measurement value can be arbitrarily set by the examiner or the assistant. In addition, it is possible to arbitrarily set how to complete the test according to changing of the answer of the person to be examined.

(Cross Cylinder Test Process)

Next, the index displayed on the index plate 43 is changed to an index S for astigmatic examination as shown in FIG. 9, that is, the index S in which a circular spot group Sa is provided in a central region thereof. Then, a cross cylinder test for measuring the astigmatic power and the astigmatic axis angle of the eye to be examined E is conducted. The Landolt ring may be used instead of the index S.

In order to measure the astigmatic axis angle of the eye to be examined E, first, the drive mechanism 49*c* is operated by the electrical component section 6 to rotate the variable cross cylinder 49. Accordingly, using the axis angle based on the objective eye examination as a reference, the cylindrical lens 49*a* that provides the refractive power of +0.25D in the +45 degree direction is disposed and the cylindrical lens 49*b* that provides the refractive power of −0.25D in the −45 degree direction is disposed. On the other hand, the liquid crystal screen 56 is changed to the screen 56*a* and the lamp 55 is turned on to operate the identifier generating optical system 18. At this time, the index S appears in the eye to be examined E, for example, in a state as shown in FIG. 10A, that is, in a state in which the identifier "1" 56*a*1 is attached to the index S. In addition to this, a voice guide is produced informing that an indicating state of the index S under the action of the variable cross cylinder 49 with such an arrangement is an index indicating state 1.

Subsequently, similarly, the arrangement directions of the pair of cylindrical lenses of the variable cross cylinder 49 are reversed in accordance with a signal from the electrical component section 6. Therefore, using the axis angle based on the objective eye examination as a reference, the cylindrical lens 49*b* that provides the refractive power of −0.25D is disposed in the +45 degree direction and the cylindrical lens 49*a* that provides the refractive power of +0.25D is disposed in the −45 degree direction. In addition, the liquid crystal screen 56 is changed to the screen 56*b*. At this time, the index S appears in the eye to be examined E, for example, in a state in which the identifier "2" 56*b*1 is attached to the index S as shown in FIG. 10B. In addition to this, a voice guide is produced informing that an indicating state of the index S under the action of the variable cross cylinder 49 with the reverse arrangement is an index indicating state 2. After that, when the index indicating state 1 can be clearly recognized, a voice guide is produced informing that it is necessary to tilt the joystick 7 to the left. On the other hand, when the index indicating state 2 can be clearly recognized, a voice guide is produced informing that it is necessary to tilt the joystick 7 to the right is produced.

Note that FIGS. 10A and 10B show visual recognition states of the person to be examined to the index S in the index indicating states 1 and 2. FIG. 10A shows a circularly recognized state in which respective spots of the spot group Sa are originally provided on the index S, that is, a state in which the astigmatism of the eye to be examined E is corrected to clearly recognize the index S. FIG. 10B shows a state in which the astigmatism of the eye to be examined E is not corrected, thereby recognizing the index S with a blurring state. Thus, in this case, the state shown in FIG. 10A is recognized as a clearly recognized side, so that the person to be examined tilts the joystick 7 to the left.

When the computer C receives a signal corresponding to the direction selected by the person to be examined, under the control of the computer C, the electrical component section 6 causes the drive mechanism 49*c* to rotate the variable cross cylinder 49 by a predetermined angle (for example, 10 degrees) according to the direction in which the joystick 7 is tilted by the person to be examined. More specifically, the variable cross cylinder 49 is rotated by a predetermined angle in a direction in which the astigmatic power set in the index indicating state on the side to which the joystick 7 is tilted (index indicating state 1 in this case) is changed in the minus direction. This step is repeated several number of times. Then, when the direction in which the joystick 7 is tilted is changed to a direction from the left to the right or a direction from the right to the left, the astigmatic axis angle measurement is completed and the astigmatic axis angle when the direction is changed is determined as a measurement value.

Note that the predetermined angle is set to 10 degrees. However, the predetermined angle can be arbitrarily set by the examiner or the like. In addition, the predetermined angle may be changed according to the result of the objective eye examination. Further, in order to improve the measurement precision, when the direction in which the joystick 7 is tilted is changed, similar measurement may be conducted using a further small rotational angle to narrow the astigmatic axis angle.

After the astigmatic axis angle is obtained, measurement of the astigmatic power is conducted. Also in this case, an index to be used is the index S. First, the variable cross cylinder 49 is rotated such that the astigmatic power of ((astigmatic power based on the objective eye examination)+(−0.25D)) acts in the direction of the obtained astigmatic axis angle and the astigmatic power of ((astigmatic power based on the objective eye examination)+(+0.25D)) acts in a direction orthogonal to the direction of the astigmatic axis angle. At the same time, the liquid crystal screen 56 is changed to the screen 56*a* and the lamp 55 is turned on to actuate the identifier generating optical system 18. The index S appears in the eye to be examined E in a state in which the identifier "1" 56*a*1 is attached to the index S. In addition, a voice guide is produced informing that an indicating state of the index S under the action of the variable cross cylinder 49 with such an arrangement is set to the index indicating state 1.

Also, the variable cross cylinder 49 is rotated such that the astigmatic power of ((astigmatic power based on the objective eye examination)+(+0.25D)) acts in the direction of the obtained astigmatic axis angle and the astigmatic power of ((astigmatic power based on the objective eye examination)+(−0.25D)) acts in a direction orthogonal to the direction of the astigmatic axis angle. In addition to this, the liquid crystal screen 56 is changed to the screen 56*b* and the index S appears in the eye to be examined E in a state in which the identifier "2" 56*b*1 is attached to the index S. In addition, a voice guide is produced informing that an indicating state of the index S under the action of the variable cross cylinder 49 with such an arrangement is set to the index indicating state 1. After that, when the index indicating state 1 can be clearly recognized, a voice guide is produced informing that it is necessary to tilt the joystick 7 to the left. On the other hand, when the index indicating state 2 can be clearly recognized, a voice guide is produced informing that it is necessary to tilt the joystick 7 to the right. Even in this case, the index is viewed by the eye to be examined E in the state shown in FIG. 10A or 10B.

The electrical component section 6 changes the astigmatic power according to the direction in which the joystick 7 is tilted by the person to be examined. More specifically, when the index indicating state 1 (FIG. 10A) is selected, the astigmatic power of −0.25D is added. When the index indicating state 2 (FIG. 10B) is selected, the astigmatic power of +0.25D is added. Such a step is repeated several number of times. Then, when the direction in which the joystick 7 is tilted is changed to a direction from the left to the right or a direction from the right to the left, the astigmatic axis angle measurement is completed. Whether the astigmatic power obtained when the direction is changed or the astigmatic power which is closer to the value obtained by the objective eye examination is determined as the measurement value can be selected by the examiner or the like.

(Spherical Power Balance Process and Both-Eye Vision Measurement Process)

After the astigmatic power and the astigmatic axis angle are obtained by the cross cylinder test, the process goes to a step of conducting the balance adjustment of the spherical powers of both eyes by a method similar to the red/green test (the index S is used as well). Because this step uses a general method, the description is omitted here. After the spherical powers of both eyes are balanced, the vision measurement is conducted in a state in which the powers obtained in all the eye examinations are used. It is finally determined whether or not the obtained powers are suitable. When the obtained powers are suitable, the eye examination is completed. When the obtained powers are not suitable, the eye examination is conducted again.

[Operation and Effect]

Now, it is rare that a remarkable difference such as that between FIG. 10A and FIG. 10B is recognized by the person to be examined in the actual eye examination. In many cases, it is difficult to distinguish which one of the index indicating states is currently selected, based on only the voice guide.

However, the identifier generating optical system 18 acts as an index identifying means that assists the person to be examined with the identification of the projection image of the index S by attaching the identifiers 56a1 and 56b1 of "1" and "2" to the pair of indicating states (index indicating state 1 and index indicating state 2) of the index S. Accordingly, the identifying power for the index indicating state is improved, so that there is no case where the person to be examined confuses both index indicating states. Thus, a delay or a mistake in a stage of selecting the index indicating state can be avoided. In addition, the voice guide produced when the index indicating state is switched can be omitted, so that a further time period reduction can be achieved. Thus, with the ophthalmologic apparatus 1, an eye examination time period is shortened, with the result that a burden on the person to be examined can be reduced and the reliability of the eye examination can be improved. If the ophthalmologic apparatus 1 is placed in a store such as a spectacle shop, the eye examination time period required for each customer is shortened to increase the flow rate of customers, thereby shortening a waiting time period, so that a burden on each customer is reduced.

Note that the person to be examined conducts actual eye examination through an exercise related to the method of operating the ophthalmologic apparatus 1, so that the voice guide with respect to the cross cylinder test can be omitted. Therefore, the eye examination time period is further shortened, with the result that a burden on the person to be examined can be further reduced. be examined.

Second Embodiment

Figure 11A:
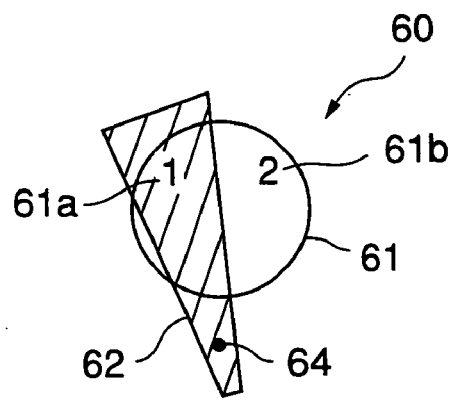
FIGS. 11A and 11b are schematic views showing a structure of an identifier displaying member included in an ophthalmologic apparatus according to a second embodiment of the present invention.
Figure 11B:
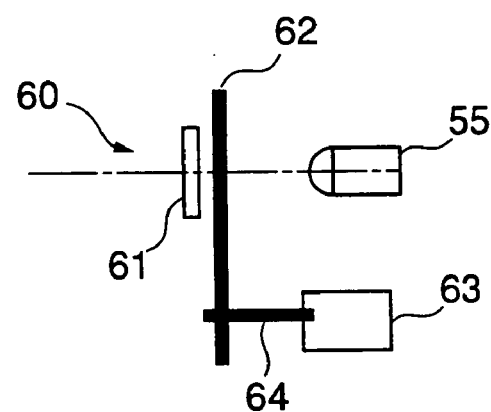

Hereinafter, a second embodiment of the present invention will be described with reference to FIGS. 11A and 11B. FIGS. 11A and 11B show an identifier displaying member 60 which is used instead of the liquid crystal screen 56 of the ophthalmologic apparatus 1. FIG. 11A is a perspective view showing a schematic structure in the case where the identifier displaying member 60 is viewed from the front side and FIG. 11B is a side view showing the schematic structure of the identifier displaying member 60. Note that FIG. 11B shows a state in which the liquid crystal screen 56 of the ophthalmologic apparatus 1 is replaced by the identifier displaying member 60. The lamp 55 and the identifier displaying member 60 compose the identification information generating means.

As shown in FIGS. 11A and 11B, the identifier displaying member 60 includes an identification index plate 61 that displays an identifier "1" 61a and an identifier "2" 61b and a shutter 62 for shielding a region of the identification index plate 61. An end portion of a rotational axis 64 of a pulse motor 63 is fixed to the shutter 62. In addition, although not shown, the pulse motor 63 operates in accordance with a signal from the electrical component section 6.

The identification index member 60 having such a structure acts as follows. First, when the signal from the electrical component section 6 is received, the pulse motor 63 rotates the rotational axis 64 in a predetermined direction by a predetermined angle. The shutter 62 rotates about the rotational axis 64 in the same direction by the same angle to shield one of the identifier "1" 61a and the identifier "2" 61b which are displayed on the identification index plate 61. That is, the predetermined angle may be approximately set to an angle formed by two line segments drawn from the rotational axis 64 to the two identifiers. When the index indicating state 1 is provided in the cross cylinder test, the predetermined direction may be controlled to be a direction in which the identifier "2" 61b is shielded. On the other hand, when the index indicating state 2 is provided, the predetermined direction may be controlled to be a direction in which the identifier "1" 61a is shielded. Therefore, even when the identification index member 60 is applied, as in the ophthalmologic apparatus 1 according to the first embodiment, the identifying power for the index indicating state is improved, the case where the person to be examined becomes confused by not being able to distinguish which is the index indicating state for the power produced is avoided. Thus, the reduction in eye examination time period and the improvement in reliability of the eye examination are achieved.

According to the first and second embodiments, the identifier is attached to each of the pair of index indicating states in the cross cylinder test. However, the identifier can be attached to only one of the pair of index indicating states. For example, a star mark is attached as the identifier to the side of the index indicating state 1, the identifier is not attached to the side of the index indicating state 2, and a voice guide "When one state to which the star mark is attached can be clearly recognized, please tilt the joystick to the left. When the other state to which the star mark is not attached can be clearly recognized, please tilt the joystick to the right." is outputted, so that the same effect can be obtained. In effect, according to the spirit of the present invention, if the identification index is attached such that the pair of index indicating states can be distinguished, the requirement is sufficiently satisfied. Therefore, as far as the requirement is satisfied, any method may be used.

Also, the pair of index indicating states can be distinguished according to a position at which the identifier is attached. For example, the identifier is attached to the left side of the index image in one index indicating state, the identifier is attached to the right side of the index image in the other index indicating state, and a voice guide is outputted urging the person to be examined to tilt the joystick to the left in the case where the former is clear and to tilt the joystick to the right in the case where the latter is clear. Thus, an object of the present invention is achieved.

Also, the identification information used in the present invention is not limited to the identifier such as the numeral, the character, or the symbol. For example, as in a third embodiment described below, a color may be provided to the index or the index indicating state to obtain an identification effect.

Third Embodiment

A purpose of the third embodiment of the present invention as described below is to improve the identifying power for the index by simultaneously projecting a fusion frame to which a color is provided and the index. The fusion frame is an index for promoting a fusion of index images respectively recognized by the left eye EL and the right eye ER in the case where the index is simultaneously projected to both eyes of the person to be examined to conduct an eye examination. Note that an ophthalmologic apparatus according to this embodiment has substantially the same structure as the first embodiment described above. Therefore, only the feature section (identifier generating optical system) will be described here.

As described above, the left eye head 3L and the right eye head 3R each include the identifier generating optical system 18. In this embodiment, a multi-color LED that conducts switching light emission using, for example, red light and green light is disposed as the lamp 55 of the identifier generating optical system 18. The switching light emission operation of the multi-color LED 55 is conducted under the control of the electrical component section 6 which receives a signal from the computer C (see FIG. 4). Here, the electrical component section 6 simultaneously conducts the control of the multi-color LED 55 included in the left eye head 3L and the control of the multi-color LED 55 included in the right eye head 3R such that both the multi-color LEDs 55 always emit the same color light.

Figure 12:
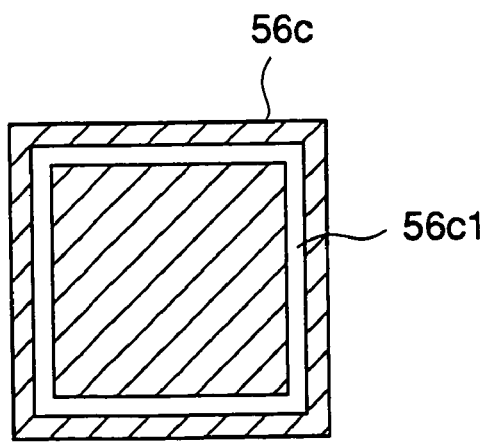
FIG. 12 is a schematic view showing a fusion frame chart displayed on a liquid crystal screen of an ophthalmologic apparatus according to a third embodiment of the present invention.

Also, a fusion frame chart 56c as shown in FIG. 12 is displayed on the liquid crystal screen 56 of the identifier generating optical system 18. A square-shaped transmission portion 56c1 is formed in the fusion frame chart 56c, so that a light flux transmitting through the transmission portion 56c1 is indicated as the fusion frame 56c1 to the person to be examined. Therefore, when red light is emitted from each of the multi-color LEDs 55 in a state in which the fusion frame chart 56c is displayed on the liquid crystal screen 56, the red fusion frame 56c1 is projected to each of the left eye EL and the right eye ER of the person to be examined. In addition, when green light is emitted from each of the multi-color LEDs 55, the green fusion frame 56c1 is projected to each of the left eye EL and the right eye ER of the person to be examined. The fusion frame 56c1 has a size enough to appear in the eye of the person to be examined in a state in which various indexes (including the Landolt ring and the index for cross cylinder test, exclusive of the fixed index) projected by the index projecting optical system 14 are surrounded by the fusion frame (see FIGS. 13A and 13B).

Figure 13A:
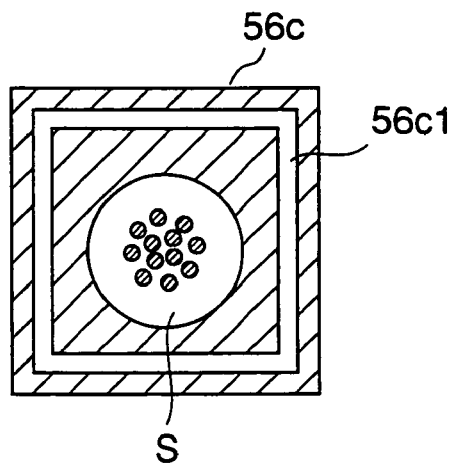
FIGS. 13A and 13B are schematic views showing indicating states of an index to the eye to be examined, which is included in the ophthalmologic apparatus according to the third embodiment.

A use state of the ophthalmologic apparatus characterized by the above-mentioned structure according to this embodiment will be described. The index for cross cylinder test is used as an index serving as an identification object. That is, the index S on the index plate 43 shown in FIG. 9 is projected as the index indicating state 1 to the left eye EL and the right eye ER of the person to be examined. In addition to this, under the control of the electrical component section 6, the fusion frame chart 56c is displayed on the liquid crystal screen 56 and red light is emitted from each of the multi-color LEDs 55. FIG. 13A shows a visual recognition state (clearly recognized state) of the person to be examined in this case. At this time, the fusion frame 56c1 is displayed with a tinge of red.

Figure 13B:
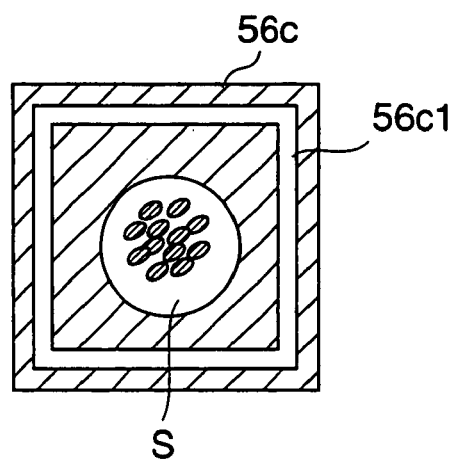

Subsequently, according to the control of the electrical component section 6, the variable cross lens 49 is reversed to project the index S as the index indicating state 2 and switching is conducted such that each of the multi-color LEDs 55 emits green light. FIG. 13B shows a visual recognition state (blurring state) of the person to be examined in this case. The fusion frame 56c1 is displayed with a tinge of green.

The index indicating state 1 and the index indicating state 2 are repeatedly indicated and a voice guide "When the red frame is clearly visible, please tilt the joystick to the left. When the green frame is clearly visible, please tilt the joystick to the right." is outputted. As a result, the person to be examined can clearly distinguish the index indicating state 1 and the index indicating state 2 from each other based on the color of the fusion frame 56c1. Thus, a reduction in eye examination precision which is caused by the confusion between the index indicating states can be eliminated. Note that, in this embodiment, the multi-color LED 55 and the liquid crystal screen 56 compose the identification information generating means.

In this embodiment, the colors of red and green are used as identification information. However, it is permissible to use other colors as a matter of course. For example, when the person to be examined has red-green color anomaly, it is an extremely natural design matter that colors other than red and green are used.

Also, in addition to the above-mentioned multi-color LED, a light source that emits a plurality of different color light fluxes which can be identified, such as a light source in which a plurality of LEDs that emit different color light fluxes are arranged, can be used as a light source for illuminating the fusion frame. In the case of such a light source, a purpose of this embodiment can be achieved without limiting the light source to a specific structure.

Also, in this embodiment, the colored fusion frame 56c1 is attached to each of the index indicating states. However, various modifications are possible. For example, only one of the index indicating states may be colored or the fusion frame 56c1 may be attached to only one of the index indicating states.

Further, a shape of the fusion frame is not limited to the square shape as in this embodiment. For example, a circular fusion frame or the like is allowed as a matter of course.

This embodiment related to the index indicating state identifying unit using the fusion frame has the following merit. That is, an ophthalmologic apparatus capable of conducting an eye examination with binocular vision generally has a function for projecting the fusion frame. Therefore, the light source for projecting the fusion frame is replaced by a light source capable of conducting switching light emission using a plurality of color light fluxes. Alternatively, a light source is constructed to be capable of switching the on/off of projection of the fusion frame according to switching between the index indicating states. When such a minimum modification of the structure is conducted, the index indicating state identifying unit using the fusion frame can be practically used.

Thus, in the respective embodiments, the index for cross cylinder test is described as the index of the identification object. However, at the time of examinations other than the cross cylinder test, in an eye examination conducted by comparing visibilities among the plurality of index indicating states successively appear in the eye to be examined, the identification information generating means and the identification information combining means are applied, so that the index indicating states can be distinguished with reliability.

Also, the ophthalmologic apparatus according to the above-mentioned embodiments is constructed so as to distinguish two kinds of indicating states of an index. However, an application scope of the present invention is not limited to such a structure. For example, in order to distinguish three or more kinds of indicating states of an index, to distinguish plural kinds of indexes, or to distinguish plural kinds of indicating states of each of plural kinds of indexes, it is possible to use the identification information generating means and the identification information combining means. In this time, an identifier displaying member including some kinds of identifiers corresponding to the number of objects to be distinguished is provided and a corresponding voice guide is produced if necessary. They are merely design matters within the spirit of the present invention.

When an ophthalmologic apparatus is considered as an example in which the identification information changing means that changes the identification information generated by the identification information generating means in accordance with changing of the index located by the index locating means is provided, the projection image of the index is combined with the identification information, and the resultant projection image is indicated to the eye to be examined, the plurality of indexes are distinguished with reliability.

Figure 14:
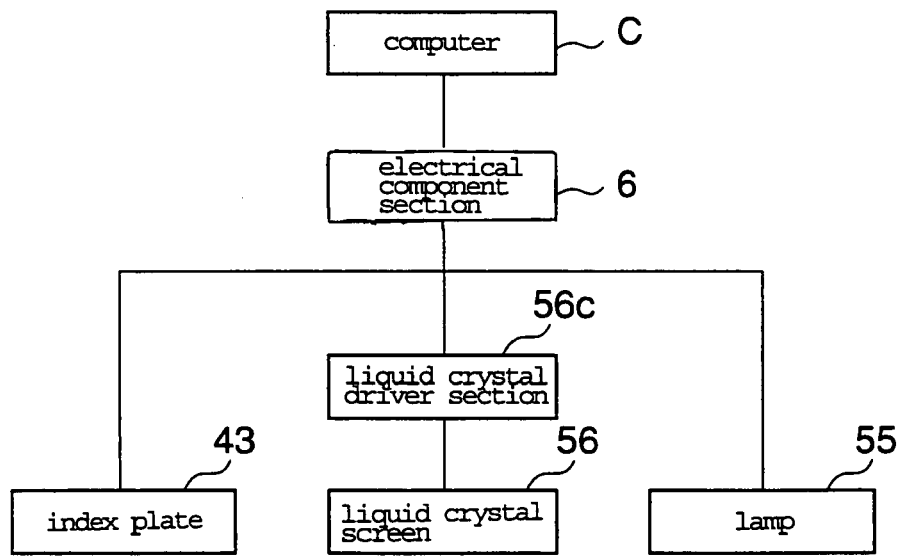
FIG. 14 is a block diagram showing a schematic structure of an ophthalmologic apparatus according to a modified example of the present invention.

In order to realize such an ophthalmologic apparatus, for example, the control of the index plate 43 which is made by the computer C and the control of the lamp 55 and the liquid crystal screen 56 in the identifier generating optical system 18 may be synchronized with each other (see FIG. 14 and further see FIG. 4). More specifically, when a first index is located on the index plate 43, the computer C outputs an instruction to the electrical component section 6 in response to the location. The electrical component section 6 causes the liquid crystal screen 56 to display first identification information (for example, the screen 56a in FIG. 8A) and causes the lamp 55 to turn on. Therefore, the first index is indicated to the eye to be examined in a state in which the first identification information is combined with the first index.

Subsequently, assume that the index located on the index plate 43 is changed and a second index is located thereon. At this time, the computer C outputs an instruction to the electrical component section 6 in response to changing of the index. The electrical component section 6 causes the liquid crystal screen 56 to change a display content thereof to second identification information (for example, the screen 56b in FIG. 8B). Therefore, the second index is indicated to the eye to be examined in a state in which the second identification information is combined with the second index.

According to the structure, it is possible that the identification information is provided to each of the plurality of different indexes to be indicated to the eye to be examined.

The ophthalmologic apparatus described in detail is just an example related to the embodiments of the present invention. Thus, it is needless to say that the spirit of the present invention is not defined based on the above-mentioned embodiments.

As described above, according to the ophthalmologic apparatus of the present invention, the identifying power for the index or the index indicating state is improved, to thereby eliminate the confusion of a person to be examined. As a result, the eye examination time period can be shortened and the reliability of the eye examination can be improved.

What is claimed is:

1. An ophthalmologic apparatus which includes index locating means capable of selectively locating an index for eye examination and an index projecting optical system that successively indicates index images to an eye to be examined by changing an index image of the index located by the index locating means, the ophthalmologic apparatus comprising:
    identification information generating means for generating identification information for making a person to be examined identify each of the index images which are successively indicated by the index projecting optical system; and
    an identification information combining member that combines the identification information generated by the identification information generating means with each of the index images to be indicated to the eye to be examined,
    wherein the identification information is a different numeral for each of a pair of index images which are indicated by reverse action of a cross cylinder.

2. An ophthalmologic apparatus according to claim 1, further comprising identification information changing means for changing the identification information generated by the identification information generating means in accordance with changing of the index image which is indicated to the eye to be examined by the index projecting optical system.

3. An ophthalmologic apparatus which includes index locating means capable of selectively locating an index for eve examination and an index projecting optical system that successively indicates index images to an eye to be examined by changing an index image of the index located by the index locating means, the ophthalmologic apparatus comprising:
    identification information generating means for generating identification information for making a person to be examined identify each of the index images which are successively indicated by the index projecting optical system;
    an identification information combining member that combines the identification information generated by the identification information generating means with each of the index images to be indicated to the eye to be examined; and
    identification information changing means for changing the identification information generated by the identification information generating means in accordance with changing of the index image which is indicated to the eye to be examined by the index projecting optical system,
    wherein the index projecting optical system comprises a cross cylinder that produces a pair of index images by providing predetermined astigmatic power to the index located by the index locating means in order to conduct an astigmatic examination on the eye to be examined, and
    the identification information changing means changes the identification information generated by identification information generating means in accordance with switching of the pair of the index images which are indicated to the eye to be examined by the cross cylinder.

* * * * *